United States Patent
Lee et al.

(10) Patent No.: US 10,480,032 B2
(45) Date of Patent: Nov. 19, 2019

(54) USE OF EI24 GENE

(71) Applicant: UNIVERSITY-INDUSTRY FOUNDATION, YONSEI UNIVERSITY, Seoul (KR)

(72) Inventors: Han Woong Lee, Seoul (KR); Jung-Min Choi, Seoul (KR); Byoung Chul Cho, Seoul (KR); Yu-Ra Choi, Gangwon-do (KR); Ji-Young Jang, Seoul (KR); Hye Ryun Kim, Seoul (KR)

(73) Assignee: University-Industry Foundation, Yonsei University (KR)

( * ) Notice: Subject to any disclaimer, the term of this patent is extended or adjusted under 35 U.S.C. 154(b) by 0 days.

(21) Appl. No.: 15/458,676

(22) Filed: Mar. 14, 2017

(65) Prior Publication Data
US 2017/0268067 A1   Sep. 21, 2017

(30) Foreign Application Priority Data

Mar. 15, 2016 (KR) ........................ 10-2016-0030852
Apr. 26, 2016 (KR) ........................ 10-2016-0050735

(51) Int. Cl.
| | | |
|---|---|---|
| *C12Q 1/68* | (2018.01) | |
| *C12Q 1/6886* | (2018.01) | |
| *G01N 33/574* | (2006.01) | |
| *A61K 31/47* | (2006.01) | |
| *A61K 31/277* | (2006.01) | |
| *A61K 38/17* | (2006.01) | |
| *A61K 45/06* | (2006.01) | |
| *A61K 31/444* | (2006.01) | |
| *A61K 31/4706* | (2006.01) | |
| *A61K 31/4709* | (2006.01) | |
| *A61K 31/517* | (2006.01) | |
| *A61K 31/5377* | (2006.01) | |

(52) U.S. Cl.
CPC .......... *C12Q 1/6886* (2013.01); *A61K 31/277* (2013.01); *A61K 31/444* (2013.01); *A61K 31/47* (2013.01); *A61K 31/4706* (2013.01); *A61K 31/4709* (2013.01); *A61K 31/517* (2013.01); *A61K 31/5377* (2013.01); *A61K 38/1709* (2013.01); *A61K 45/06* (2013.01); *G01N 33/57496* (2013.01); *C12Q 2600/106* (2013.01); *C12Q 2600/158* (2013.01); *G01N 33/57423* (2013.01)

(58) Field of Classification Search
CPC ........... C12Q 1/6869; C12Q 2600/158; A61K 39/00; A61K 31/277; A61K 38/1709
See application file for complete search history.

(56) References Cited

U.S. PATENT DOCUMENTS 5,843,659 A * 12/1998 Lehar ................. C07K 14/4747
                                                          435/6.13

FOREIGN PATENT DOCUMENTS

KR          101213033 B1      12/2012

OTHER PUBLICATIONS

Mork et al in "Loss of putative tumor suppressor EI24/PIG8 confers resistance to etoposide" (FEBS Letters vol. 581, 2007: pp. 5440-5444), (Year: 2007).*
Nguyen et al (Clinical Lung Cancer, 2009, vol. 10, No. 4, pp. 281-289) (Year: 2009).*
Uramoto et al in "Expression of selected gene for acquired drug resistance to EGFR-TKI in lung adenocarcinoma" (Lung Cancer 2011 vol. 73: pp. 361-365), (Year: 2011).*
Pelod in "Insulin-like growth factor-1 receptor (IGF-1R) as a biomarker for resistance to the tyrosine kinase inhibitor gefitinib in non-small cell lung cancer" (Cell Oncol; Jul. 2013, vol. 36, No. 4: pp. 277-288). (Year: 2013).*
Choi, Publication of Graduate thesis, The Graduate School, Yonsei University, Department of Biochemistry, "The Role of EI24 in the Regulation of Tumor Metastasis and Drug Resistance", Mar. 16, 2015, Translation, 143 pages.
Choi et al., "Reduced expression of EI24 confers resistance to gefitinib through IGF-1R signaling in PC9 NSCLC cells", Lung Cancer 90 (2015) 175-181.

* cited by examiner

*Primary Examiner* — Catherine S Hibbert
(74) *Attorney, Agent, or Firm* — Adsero IP (57) ABSTRACT

The present disclosure relates to a novel use of EI24, and provides a novel use of EI24 involved in the improvement of EGFR-TKI drug resistance by inhibiting IGF-1R signaling. According to the present disclosure, the presence or absence of resistance to anti-cancer drugs may be determined by detecting an expression level of EI24. In addition, resistance to anti-cancer drugs may be inhibited, delayed, or improved using EI24 or an activating agent thereof. Moreover, by regulating a pathway of EI24-mediated resistance to anti-cancer drugs, the efficacy of existing anti-cancer drugs may be enhanced, and resistance to anti-cancer drugs may be inhibited, delayed, or improved.

3 Claims, 6 Drawing Sheets
Specification includes a Sequence Listing.

SEQUENCE LISTING

```
<160> NUMBER OF SEQ ID NOS: 2

<210> SEQ ID NO 1
<211> LENGTH: 59
<212> TYPE: DNA
<213> ORGANISM: Artificial sequence
<220> FEATURE:
<223> OTHER INFORMATION: #TRCN0000159876: shRNA
<300> PUBLICATION INFORMATION:
<301> AUTHORS: Han-Woong Lee et al.
<302> TITLE: Reduced expression of EI24 confers resistance to gefitinib
      through IGF-IR signaling in PC9 NSCLC cells
<303> JOURNAL: Lung Cancer
<304> VOLUME: 90
<306> PAGES: 175-181
<307> DATE: 2015-09-03
<300> PUBLICATION INFORMATION:
<301> AUTHORS: Jung-Min Choi
<302> TITLE: The role of EI24 in the regulation of tumor metastasis and
      drug resistance
<307> DATE: 2015-03-16

<400> SEQUENCE: 1
ccgggccatt tggtttcagg atatactcga gtatatcctg aaaccaaatg gcttttttg        59

<210> SEQ ID NO 2
<211> LENGTH: 59
<212> TYPE: DNA
```

```
<213> ORGANISM: Artificial sequence
<220> FEATURE:
<223> OTHER INFORMATION: #TRCN0000160559: shRNA
<300> PUBLICATION INFORMATION:
<301> AUTHORS: Han-Woong Lee et al.
<302> TITLE: Reduced expression of EI24 confers resistance to gefitinib
      through IGF-IR signaling in PC9 NSCLC cells
<303> JOURNAL: Lung Cancer
<304> VOLUME: 90
<306> PAGES: 175-181
<307> DATE: 2015-09-03
<300> PUBLICATION INFORMATION:
<301> AUTHORS: Jung-Min Choi
<302> TITLE: The role of EI24 in the regulation of tumor metastasis and
      drug resistance
<307> DATE: 2015-03-16

<400> SEQUENCE: 2
ccggcaaagc atatctcttc cagttctcga gaactggaag agatatgctt tgttttttg    59
```

USE OF EI24 GENE

CROSS-REFERENCE TO RELATED APPLICATION

This application claims priority to and the benefit of Korean Patent Application No. 10-2016-0030852, filed on Mar. 15, 2016, and 10-2016-0050735, filed on Apr. 26, 2016, the disclosure of which is incorporated herein by reference in its entirety.

SEQUENCE STATEMENT

Incorporated by reference herein in its entirety is the Sequence Listing entitled "G16U16C0322P-US_sequence_listing_ST25," created Mar. 14, 2017, size of 2 kilobyte.

BACKGROUND

Field of the Invention

The present invention relates to a novel use of Etoposide-induced protein 2.4 homolog (EI24) involved in the improvement of Epidermal Growth Factor Receptor Tyrosine Kinase Inhibitor (EGFR-TKI) drug resistance by inhibiting Insulin growth factor-1 receptor (IGF-1R) signaling.

Discussion of Related Art

Cancer-related research has been rapidly advanced for the last several decades and thus most cancers can be completely cured when detected early. Recently, through understanding of molecular biological mechanisms instead of existing chemotherapy, receptor tyrosine kinase (RTK) inhibitors using such molecular biological mechanisms have been used as a core technique for targeted treatments, and many pharmaceutical firms actually have released RTK drugs for various carcinomas. While such targeted therapies exhibit significant effects for a certain period of time, the therapies ultimately exhibit resistance to anticancer drugs and rather aggressive behaviors. Thus, overcoming resistance to anticancer drugs still remains elusive in cancer treatment fields.

Meanwhile, EI24 is a p53-responsive gene and known as a pro-apoptotic gene that induces apoptosis. EI24 genes are known to play an important role in carcinogenesis and metastasis, and thus research thereinto is actively ongoing. The inventors of the present application have already discovered a correlation between the EI24 gene and protein expression levels and metastasis through previous research (Korean Patent No. 10-1213033).

However, the use of EI24 related to anticancer drug resistance is not known to date.

SUMMARY OF THE INVENTION

The present invention is directed to a use of EI24 whereby the presence or absence of resistance to anticancer drugs may be predicted, and a use of EI24 or an activating agent thereof to inhibit or improve anticancer drug resistance.

According to an aspect of the present invention, there is provided a composition for identifying Epidermal Growth Factor Receptor Tyrosine Kinase Inhibitor (EGFR-TKI) drug resistance, including: a primer or probe specifically binding to EI24 gene; or an antibody specifically binding to EI24 protein.

According to another aspect of the present invention, there is provided a kit for identifying EGFR-TKI drug resistance, including the above-described composition.

According to still another aspect of the present invention, there is provided a method of detecting EI24 in an EGFR-TKI drug-administered patient, including: contacting a biological sample from an EGFR-TKI drug-administered patient with a primer or probe specifically binding to the EI24 gene, and detecting an expression level of EI24 in the biological sample by detecting the binding between the EI24 gene and the primer or the probe.

According to yet another aspect of the present invention, there is provided a method of detecting EI24 in an EGFR-TKI drug-administered patient, including: contacting a biological sample from an EGFR-TKI drug-administered patient with an antibody specifically binding to EI24 protein and detecting an expression level of EI24 in the biological sample by detecting the binding between the EI24 protein and the antibody.

According to yet another aspect of the present invention, there is provided a method of diagnosing and treating EGFR-TKI drug resistance in an EGFR-TKI drug-administered patient, including: contacting a biological sample from an EGFR-TKI drug-administered patient with a primer or probe specifically binding to EI24 gene, and detecting an expression level of EI24 in the biological sample by detecting the binding between the EI24 gene and the primer or the probe; diagnosing the EGFR-TKI drug-administered patient as having EGFR-TKI drug resistance when the expression level of EI24 is 5 times to 20 times lower than that of a control sample obtained from an EGFR-TKI drug resistance-free control group; and administering an effective amount of EI24 to the patient diagnosed as having EGFR-TKI drug resistance.

According to yet another aspect of the present invention, there is provided a method of diagnosing and treating EGFR-TKI drug resistance in an EGFR-TKI drug-administered patient, including: contacting a biological sample from an EGFR-TKI drug-administered patient with an antibody specifically binding to EI24 protein, and detecting an expression level of EI24 in the biological sample by detecting the binding between the EI24 protein and the antibody; diagnosing the EGFR-TKI drug-administered patient as having EGFR-TKI drug resistance when the expression level of EI24 is 5 times to 20 times lower than that of a control sample obtained from an EGFR-TKI drug resistance-free control group; and administering an effective amount of EI24 to the patient diagnosed as having EGFR-TKI drug resistance.

According to yet another aspect of the present invention, there is provided a pharmaceutical composition for inhibiting, improving, or treating EGFR-TKI drug resistance, including EI24 gene, an EI24 gene expression activating agent EI24 protein, or an EI24 protein activating agent.

According to yet another aspect of the present invention, there is provided a method of treating a patient having EGFR-TKI drug resistance, including administering an effective amount of EI24 to the patient having EGFR-TKI drug resistance.

According to yet another aspect of the present invention, there is provided a pharmaceutical composition for inhibiting IGF-1R signaling, including EI24 gene, an EI24 gene expression activating agent, EI24 protein, or an EI24 protein activating agent.

According to yet another aspect of the present invention, there is provided a method of screening a drug for inhibiting, improving, or treating EGFR-TKI drug resistance, including: contacting a candidate with an EGFR-TKI-resistant cell line, and detecting an expression level of EI24 in the EGFR-TKI-resistant cell line; and determining that, when the expression level of EI24 in the EGFR-TKI-resistant cell line is 5 times to 20 times higher than that before being in contact with the candidate, the candidate is a drug for inhibiting, improving, or treating EGFR-TKI drug resistance.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, the present invention will be described with reference to examples and comparative examples in detail. However, the present invention is not limited to these examples.

Hereinafter, configurations of the invention will be described in detail.

The present disclosure relates to a composition for identifying Epidermal Growth Factor Receptor Tyrosine Kinase Inhibitor (EGFR-TKI) drug resistance, including: a primer or probe specifically binding to EI24 gene; or an antibody specifically binding to EI24 protein.

The present disclosure also provides a method of detecting EI24 in an EGFR-TKI drug-administered patient, including: contacting a biological sample from an EGFR-TKI drug-administered patient with a primer or probe specifically binding to EI24 gene, and detecting an expression level of EI24 in the biological sample by detecting the binding between the EI24 gene and the primer or the probe.

The present disclosure also provides a method of detecting EI24 in an EGFR-TKI drug-administered patient, including: contacting a biological sample from an EGFR-TKI drug-administered patient with an antibody specifically binding to EI24 protein, and detecting an expression level of EI24 in the biological sample by detecting the binding between the EI24 protein and the antibody.

As used herein, the primer or probe specifically binding to EI24 gene; or the antibody specifically binding to EI24 protein means an agent for measuring the expression level of EI24.

The term "024" as used herein, which does not distinguish the EI24 gene from the EI24 protein, is interpreted as including both the EI24 gene and the EI24 protein. In addition, EI24, EI24 gene, or EI24 protein is interpreted as including a fragment thereof having substantially the same activity. Thus, the expression level of EI24 is interpreted as including an expression level of mRNA of the EI24 gene or an expression level of the EI24 protein obtained therefrom.

In one embodiment, an agent for specifying the expression level of mRNA of the EI24 gene includes, but is not limited to, a primer or probe specifically binding to the EI24 gene.

The term "probe" as used herein means a nucleic acid fragment such as RNA, DNA, or the like in length from several bases up to several hundred bases that can be specifically bound to mRNA. Non-limiting examples of suitable probes include oligonucleotide probes, single-stranded DNA probes, double-stranded DNA probes, and RNA probes, which are labeled to detect the presence or absence of a specific mRNA.

The term "primer" as used herein indicates a short nucleic acid sequence having a short free 3'-terminal hydroxyl group that can form base pairs with a complementary template and function as an initiation point for template strand replication. The primer may initiate DNA synthesis in the presence of a reagent for polymerization in an appropriate buffer and at an appropriate temperature (DNA polymerase or reverse transcriptase) and four different deoxynucleoside triphosphates (dNTPs). The primer of the present disclosure is a primer specifically binding to the EI24 gene and may be, for example, a primer composed of sense (forward) and antisense (backward) nucleic acids having a sequence of 7 to 50 nucleotides. The primer may have additional characteristics so long as it can function as an initiation point of DNA synthesis, which is the basic characteristic thereof. In addition, if desired, the nucleotide sequence of the primer of the present disclosure may include a marker that can be detected directly or indirectly by spectroscopic, photochemical, biochemical, immunochemical or chemical means.

In one embodiment, the primer may be a sense and/or antisense primer complementary to mRNA of the EI24 gene. The primer may include a sense or antisense primer alone or include sense and antisense primers together.

The primer or probe according to the present disclosure may be chemically synthesized using a known method.

In one embodiment, the EGFR-TKI may be at least one selected from erlotinib, lapatinib, apatinib, neratinib, poziotinib, and gefitinib.

The present disclosure also provides a kit or system for identifying EGFR-TKI drug resistance, including the above-described composition.

In one embodiment, the kit includes general mRNA and protein quantification-based diagnostic kits without particular limitation. For example, the kit may be an RT-PCR kit, a DNA chip kit, a protein kit, or an array kit. When an RT-PCT kit is used, the RT-PCT kit may include, in addition to each primer pair specific to the EI24 gene, a test tube or other appropriate containers, a reaction buffer, deoxynucleoside triphosphates (dNTPs), an enzyme such as Taq-polymerase and reverse transcriptase, DNase and RNase inhibitors, sterilized water, or the like.

The present disclosure also provides a method of diagnosing and treating EGFR-TKI drug resistance in an EGFR-TKI drug-administered patient, including: contacting a biological sample from an EGFR-TKI drug-administered patient with a primer or probe specifically binding to EI24 gene, and detecting an expression level of EI24 in the biological sample by detecting the binding between the EI24 gene and the primer or the probe; diagnosing the EGFR-TKI drug-administered patient as having EGFR-TKI drug resistance when the expression level of EI24 is 5 times to 20 times lower than that of a control sample obtained from an EGFR-TKI drug resistance-free control group; and administering an effective amount of EI24 to the patient diagnosed as having EGFR-TKI drug resistance.

The present disclosure also provides a method of diagnosing and treating EGFR-TKI drug resistance in an EGFR-TKI drug-administered patient, including: contacting a biological sample from an EGFR-TKI drug-administered patient with an antibody specifically binding to EI24 protein, and detecting an expression level of EI24 in the biological sample by detecting the binding between the EI24 protein and the antibody; diagnosing the EGFR-TKI drug-administered patient as having EGFR-TKI drug resistance when the expression level of EI24 is 5 times to 20 times lower than that of a control sample obtained from an EGFR-TKI drug resistance-free control group; and administering an effective amount of EI24 to the patient diagnosed as having EGFR-TKI drug resistance.

In one embodiment, the biological sample may be blood or a biopsy tissue.

Exemplary detection methods of the expression level of mRNA of the EI24 gene include, but not limited to, RT-PCR, competitive RT-PCR, RNase protection assay, Northern blotting, a DNA chip, NanoString technology, RNA assay using RNA sequences, or the like. Through the above-described detection methods, an expression amount of mRNA of a biological sample from an individual needed to determine the presence or absence of drug resistance and an expression amount of mRNA in a control sample may be identified, and the presence or absence of EGFR-TKI drug resistance may be determined by comparing the expression amounts thereof.

In one embodiment, when the expression level of mRNA of the EI24 gene of a biological sample or the expression level of the protein obtained therefrom is lower than that of a control sample, it may be a marker for the determination of EGFR-TKI drug resistance.

In one embodiment, the EGFR-TKI may be at least one selected from erlotinib, lapatinib, apatinib, neratinib, poziotinib, and gefitinib.

The present disclosure also provides a pharmaceutical composition for inhibiting, improving, or treating EGFR-TKI drug resistance, including EI24 gene, an EI24 gene expression activating agent, EI24 protein, or an EI24 protein activating agent.

The present disclosure also provides a method of treating a patient having EGFR-TKI drug resistance, including administering an effective amount of EI24 to the patient having EGFR-TKI drug resistance.

When the patient has drug resistance as compared to a control sample, the expression level of EI24 gene or EI24 protein is lowered, and thus the drug resistance may be delayed, inhibited, improved, or treated by increasing the expression level thereof to a normal level.

In one embodiment, the EGFR-TKI may be at least one selected from erlotinib, lapatinib, apatinib, neratinib, poziotinib, and gefitinib.

The inventors of the present disclosure investigated what mechanism contributes to a correlation between the EI24 expression level and the EGFR-TKI drug resistance. As a result, they confirmed that EI24 is involved in EGFR-TKI drug resistance through the IGF-1R signaling pathway. In particular, it is confirmed that, when the expression level of EI24 is decreased, IGF-1R signaling is activated and, accordingly, EGFR-TKI drug resistance is generated. Thus, when the expression of EI24 is increased using EI24 gene, an EI24 gene expression activating agent, EI24 protein, an EI24 protein activating agent, or the like, the activation of the IGF-1R signaling according to reduced EI24 expression may be inhibited.

Thus, a delaying, inhibiting, improving or treating effect of the EGFR-TKI drug resistance may be enhanced by administering at least one selected from the group consisting of EGFR-TKI and IGF-1R inhibitors together with EI24 gene, an EI24 gene expression activating agent, EI24 protein, or an EI24 protein activating agent to the patient having EGFR-TKI drug resistance.

Non-limiting examples of the IGF-1R inhibitor include OSI-906, NVP-AEW541, GSK1904529A, NVP-ADW742, BMS-536924, NT157, AG-1024, GSK1838705A, BMS-754807, PQ401, and picropodophyllin.

The present disclosure also provides a pharmaceutical composition for inhibiting IGF-1R signaling, including EI24 gene, an EI24 gene expression activating agent, EI24 protein, or an EI24 protein activating agent.

In one embodiment, the inhibition of the IGF-1R signaling may be performed to inhibit or improve EGFR-TKI drug resistance. When the activation of the IGF-1R signaling according to reduced EI24 expression is inhibited, the EGFR-TKI drug resistance may be consequently delayed, inhibited, or improved.

The present disclosure also provides a composition for screening an IGF-1R signaling-inhibiting drug, including EI24 gene or EI24 protein.

The present disclosure also provides a method of screening a drug for inhibiting, improving, or treating EGFR-TKI drug resistance, including: contacting a candidate with an EGFR-TKI-resistant cell line, and detecting an expression level of EI24 in the EGFR-TKI-resistant cell line; and determining that, when the expression level of EI24 in the EGFR-TKI-resistant cell line is 5 times to 20 times higher than that before being in contact with the candidate, the candidate is a drug for inhibiting, improving, or treating EGFR-TKI drug resistance.

As described above, an increase in the expression level of the EI24 gene or EI24 protein may inhibit the activation of the IGF-1R signaling, and thus a material that accelerates the expression level of the EI24 gene or EI24 protein may be used as a drug for inhibiting the IGF-1R signaling.

A reaction between the EI24 and the candidate may be identified using one of general methods used to identify the presence or absence of a reaction between a protein and a protein, between a protein and a compound, between DNA and DNA, between DNA and RNA, between DNA and a protein, between DNA and a compound, between RNA and a protein, or between RNA and a compound. Non-limiting examples of the general methods include: an in vitro hybridization test for identifying the presence or absence of binding between the EI24 gene and a candidate; Northern analysis after the reaction between a mammalian cell and a test target material; a method of measuring an expression rate of the gene by quantitative PCR, quantitative real-time PCR, or the like; a method of measuring an expression rate of a reporter protein, after linking a reporter gene to the above-described gene to be introduced into a cell and then reacting the introduced resulting gene with a test target material, by quantitative PCR, quantitative real-time PCR; a method of measuring activity after the reaction between the EI24 protein and a candidate; yeast two-hybridization; searching for phage-displayed peptide clones binding to the EI24 protein; high throughput screening (HTS) using natural and chemical libraries, or the like; drug hit HTS; cell-based screening; and DNA array-using screening.

The composition for screening may further include, in addition to the EI24, distilled water or a buffer that stably maintains a structure of nucleic acids or proteins. In addition, for an in vivo experiment, the composition for screening may include a cell expressing the EI24, a cell including an EI24-expressing plasmid in the presence of a promoter capable of modulating a transcription rate, or the like. In addition, the composition for screening may further include, in addition to the EI24, Dv1 according to a method of identifying the reaction between EI24 and a candidate.

In the screening method of the present disclosure, the test target material is assumed to have a possibility as a drug that inhibits IGF-1R signaling according to a general selecting method or may be randomly selected individual nucleic acids, protein, other extracts or natural substances, compounds, or the like.

The advantages and features of the present disclosure and the manner of achieving them will become apparent with reference to examples described below in detail. The application may, however, be embodied in many different forms and should not be construed as being limited to the examples set forth herein; rather, these examples are provided so that this disclosure will be thorough and complete, and will fully convey the scope of the invention to those of ordinary skill in the art. The present disclosure should be defined by the scope of the claims.

EXAMPLES (Cell Culture and Establishment of Cell Lines)

A PC9 EGFR-mutant NSCLC cell line and its gefitinib-resistant derivative (PC9-GR) are described in a document by S. M. Kim et al. (*Mol. Cancer Ther. vol.* 11, pp. 2254-2264(2012)). All cells were cultured in an RPMI 1640 medium supplemented with 10% PBS. A human EI24-overexpressing cell line and a control cell line were established by transfection with a plasmid including FLAG-tagged EI24 and the corresponding empty vector (pcDNA3.1), respectively. Human EI24-knockdown cell lines were established using a method described in a document by J. M. Choi et al. (*Oncotarget, vol.* 4, pp. 2383-2396 (2013)). The shRNA sequences are as follows:

```
#TRCN0000159876:
                                        (SEQ ID NO: 1)
5'-
CCGGGCCATTTGGTTTCAGGATATACTCGAGTATATCCTGAAACCAAATG
GCTTTTTTG-3';
and

#TRCN0000160559:
                                        (SEQ ID NO: 2)
5'-
CCGGCAAAGCATATCTCTTCCAGTTCTCGAGAACTGGAAGAGATATGCTT
TGTTTTTTG-3'.
```

(Plasmids and Reagents)

A human EI24 construct is described in a document by J. M. Choi et al. (*Oncotarget, vol.* 4, pp. 2383-2396(2013)). shRNAs against human EI24 were purchased from Sigma-Aldrich, gefitinib was purchased from Cayman Chemical, PQ-401 and AG-1024 were purchased from Selleck Chemicals, and human IGF-1 and recombinant IGF-1 were purchased from R&D Systems.

(Immunoblotting and Antibodies)

Protein extraction was performed as described in a document by S. Devkota et al. (*Int. J. Biochem. Cell Biol. vol.* 44, pp. 1887-1896(2012)). The immunoblotting results were obtained using a LAS-3000 Imager (available from Fujifilm). For this, the following antibodies were used: anti-phospho-EGFR, anti-EGFR, anti-phospho-IRS-1, anti-IRS-1, anti-AKT, anti-phospho-AKT, anti-ERK1/2, and anti-phospho-ERK1/2. The antibodies were purchased from Cell Signaling Technology.

(RNA Isolation and Real-Time qPCR)

Total RNA was prepared using TRIzol (Invitrogen). 1 µg of total RNA was reverse-transcribed to cDNA using the Superscript III First-Strand Synthesis System with Oligo-dT primers (Invitrogen). Real-time qPCR was performed as described in a document by J. M. Choi et al. (*Oncotarget, vol.* 4, pp. 2383-2396(2013)). Primer sequences described in the above document were used or primer sequences used were obtained from OriGene (www.origene.com).

(Cell Viability Assay)

Cells were seeded at a density of $3 \times 10^4$ cells/well in a 96-well culture plate and incubated for 24 hours. The cells were exposed to drugs for 48 hours, and 0.4 mg/ml MTT was added until reaching a mid-height of each well. After incubating at 37° C. for 4 hours, formazan crystals in viable cells were solubilized with 100 µl of dimethyl sulfoxide (DMSO). The optical density of the formazan product was read at 590 nm on a microreader (Bio-Rad). All experiments were repeated three times.

(IGF-1 Quantification)

Supernatants were collected from cultured cells and centrifuged for 5 minutes to remove dead cells and cellular debris. Enzyme-linked immunosorbent assay (ELISA) for IGF-1 was conducted using a kit (#DG100, R&D Systems) according to the manufacturer's instructions.

(Human RTK And Kinase Assay)

Proteome profiler human phospho-RTK antibody assay and human phospho-kinase antibody assay kits (R&D Systems) were used according to the manufacturer's instructions. Briefly, fresh proteins were incubated overnight at 4°

C. with nitrocellulose membranes dotted with duplicate antibody spots for 49 RTKs (RTK assay) or 43 kinases and two related total proteins (kinase assay), each including reference controls. The bound proteins were detected with 50 μl of mouse anti-phospho-tyrosine antibodies conjugated to horseradish peroxidase (HRP) by chemiluminescence assay.

(GEO2R Analysis)

Microarray datasets including gene expression values of EGFR-TKI-sensitive and EGFR-TKI-resistant clones were obtained from Gene Expression Omnibus (www.ncbi.nlm nih.gov/geo). Among these datasets, the GSE38121 dataset (Z. Zhang et al. *Nat. Genet. vol.* 44, pp. 852-860(2012)), the GSE38404 dataset (A. B. Cortot et al. *Cancer Res. vol.* 73, pp. 834-843(2013)), and the GSE37700 dataset (D. Ercan et al. *Cancer Discov. vol.* 2, pp. 934-947(2012)) were selected to evaluate the expression of EI24. The data were analyzed through the GEO2R interface as described in a document by T. Barrett et al. (*Nucleic Acids Res. vol.* 41, pp.D991-D995 (2013)).

(Statistical Snalysis)

Statistical analysis was performed using GraphPad Prism. Unpaired t-tests were used, unless otherwise stated. Values of $P<0.05$ were considered statistically significant.

<Example 1> Analysis of Correlation Between EI24 Expression Level and Resistance to EGFR-TKI To predict a role of EI24 with respect to EGFR-TKI, expression amounts of EI24 were compared through several reference documents, describing microarray results of EGFR-TKI-sensitive and EGFR-TKI-resistant cells for each of a plurality of generations (first to third generations), and Oncomine data analysis results.

Figure 1:
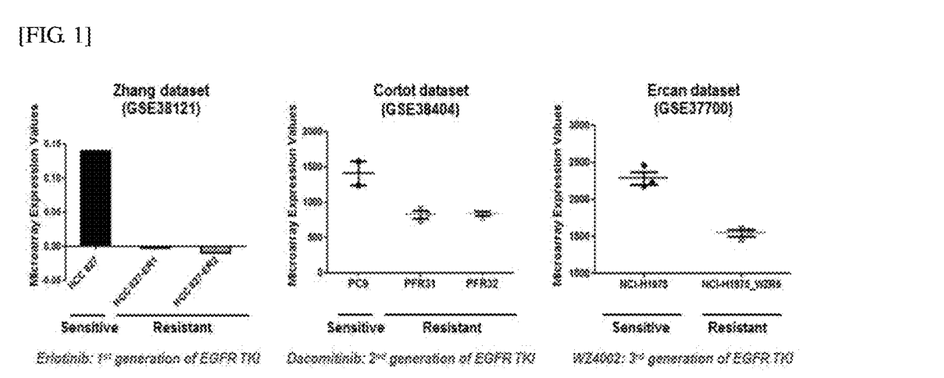
FIG. 1 illustrates comparison results of expression levels of EI24 according to the presence or absence of resistance to EGFR-TKI.

In FIG. 1, the Zhang dataset (GSE38121) shows EI24 gene expression values in erlotinib-sensitive HCC827 cells and erlotinib-resistant clones HCC827-ER1 and HCC827-ER2, and the Cortot dataset (GSE38404) and the Ercan dataset (GSE37700) show EI24 gene expression values in drug-sensitive clones (PC9 and NCI-H1975) and drug-resistant clones (PFR31, PFR32, and NCI-H1975-WZR6).

As shown in FIG. 1, it was confirmed that the expression amount of EI24 was lower in the EGFR-TKI-resistant cells for each generation than in the EGFR-TKI-sensitive cells for each generation.

Based on the above-described results, it was observed through real-time qPCR analysis whether sensitivity to the corresponding drug was changed when EI24 expression was lowered using shRNA in EGFR-mutant and EGFR-TKI (gefitinib)-sensitive non-small cell lung cancer cell lines PC9.

The shRNA includes a GFP-targeting sequence (9-shGFP) and EI24-targeting sequences (9-shEI24#1 and 9-shEI24#2).

Figure 2:
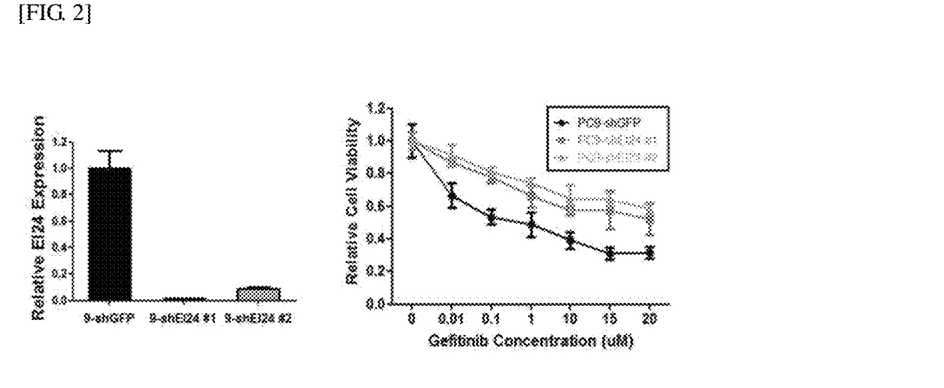
FIG. 2 illustrates comparison results of gefitinib sensitivity according to reduced EI24 expression in lung cancer cell lines.

As shown in FIG. 2, it was observed that an $IC_{50}$ value of PC9, which is a non-small cell lung cancer cell line, was about 0.1 μM, while the $IC_{50}$ value was obtained at a concentration of at least 100 times or more when EI24 expression was decreased. Thus, an increase in EGFR-TKI resistance was confirmed when EI24 expression was decreased in EGFR-mutant non-small cell lung cancer, which is consistent with microarray data obtained by other research groups.

In addition, the EI24 gene was over-expressed in a gefitinib-resistant cell line (PC9-GR) among PC9 cell lines and gefitinib was added thereto, and EI24 expression and apoptosis were measured through immunoblotting analysis and MTT assay, respectively. In the immunoblotting analysis for EI24 expression in the PC9-GR cells, the PC9-GR cells express a control vector (9GR-Ctrl) or exogenous EI24 (9GR-O/E#1 and #2).

Figure 3:
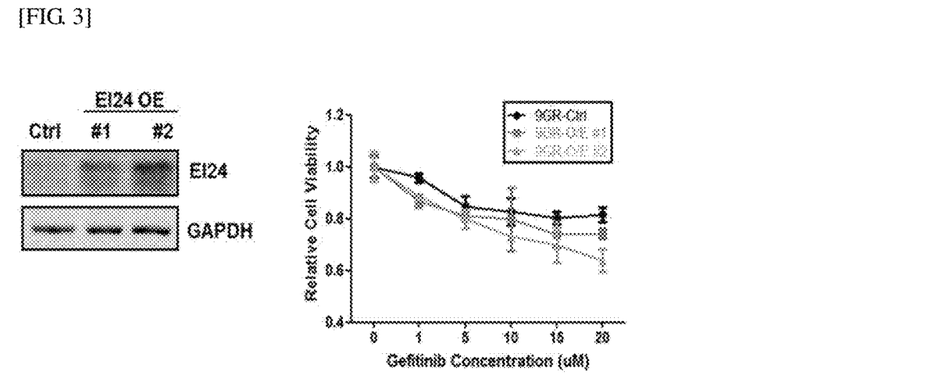
FIG. 3 illustrates comparison results of gefitinib sensitivity according to overexpression of EI24 in lung cancer cell lines.

As shown in FIG. 3, increased sensitivity to gefitinib was observed. In addition, ectopic expression of EI24 reduced cell viability up to 18% upon exposure to 20 μM gefitinib.

To identify the molecular mechanism of 024-mediated EGFR-TKI sensitivity, protein phosphorylation of EGFR, AKT, and ERK1/2 were tested after treating EI24 knock-down cells (9-shEI24) and control cells (9-shGFP) with gefitinib.

Figure 4:
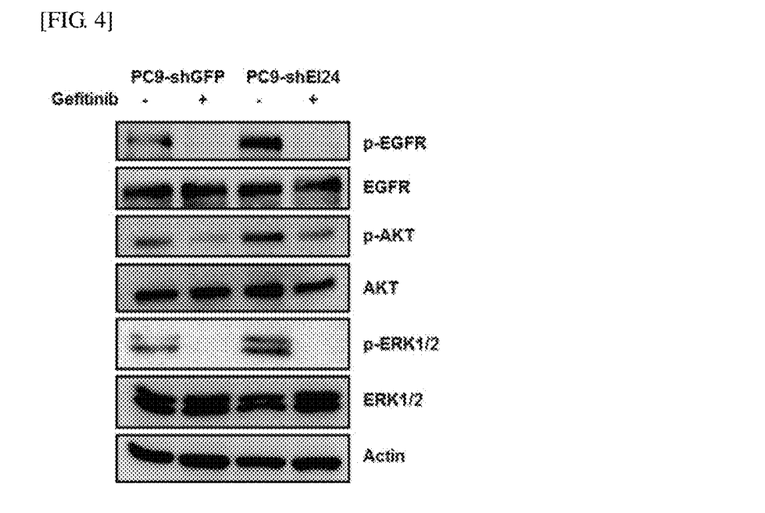
FIG. 4 illustrates comparison results of expression levels of signaling molecules according to reduced EI24 expression in lung cancer cell lines.

9-shEI24 cells exhibited increased expression of p-EGFR, p-AKT, and p-ERK1/2 as compared to the control cells, from which is confirmed that reduced EI24 expression activated EGFR through the phosphorylation of EGFR, while it did not block the phosphorylation of EGFR, which is a mechanism of action of gefitinib (see FIG. 4).

Figure 5:
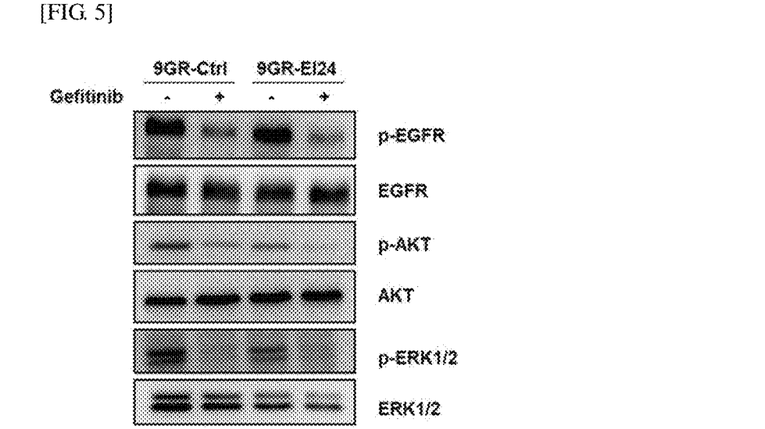
FIG. 5 illustrates comparison results of expression levels of signaling molecules according to overexpression of EI24 in gefitinib-resistant lung cancer cell lines.

In addition, it was observed whether the AKT phosphorylation was diminished by ectopic expression of EI24 upon treatment with gefitinib in PC9-GR cells. As a result, the activation of AKT, which is one signal for viability of non-small cell lung cancer cell lines, was still maintained, and the activation of AKT was decreased when EI24 was over-expressed in gefitinib-resistant cell lines (see FIG. 5).

<Example 2> Analysis of Acquired Drug Resistance Mechanism According to Reduced EI24 Expression RTK array was performed to observe an acquired resistance mechanism according to reduced EI24 expression, and it was observed that the reduced EI24 expression induced activation of IGF-1R and inhibited over-expression thereof.

Figure 6:
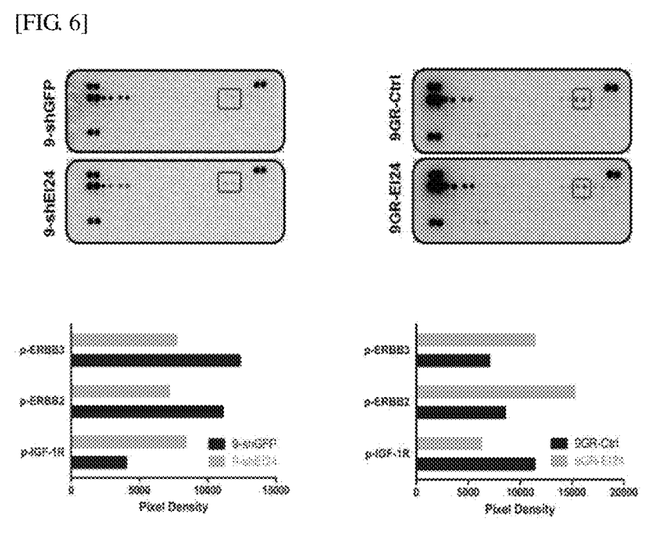
FIG. 6 illustrates test results of a receptor tyrosine kinase (RTK) array used to analyze an acquired drug resistance mechanism according to reduced EI24 expression.

To identify the presence or absence of kinase switching, which is one acquired RTK drug resistance mechanism, RTKs activated by genetic changes of EI24 were screened through RTK array using Proteome Profiler Human Phospho-RTK Antibody Array and Human Phospho-Kinase Antibody Array kits (R&D Systems) and, as a result, it was observed that the activation of IGF-1R was specifically changed by EI24 (see FIG. 6).

Figure 7:
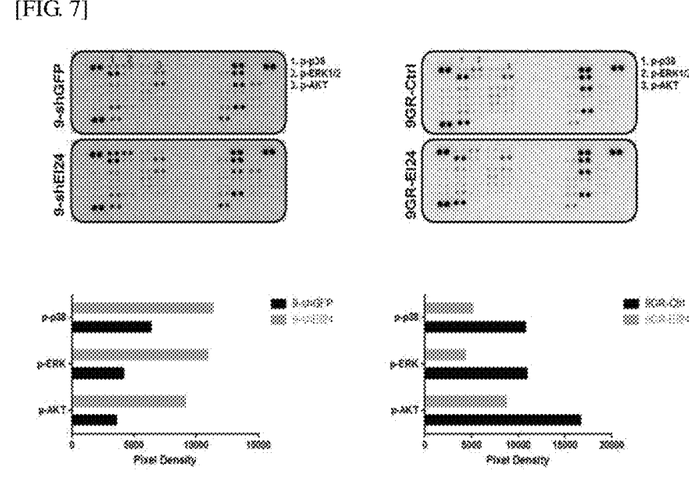
FIG. 7 illustrates analysis results of activation of molecules downstream of IGF-1R according to reduced EI24 expression.

In addition, activation changes of molecules downstream of IGF-1R activated by the EI24 gene were examined through the same array experiment and, as a result, regulation of the activation of AKT, ERK1/2, p38, and the like was observed (see FIG. 7).

Figure 8:
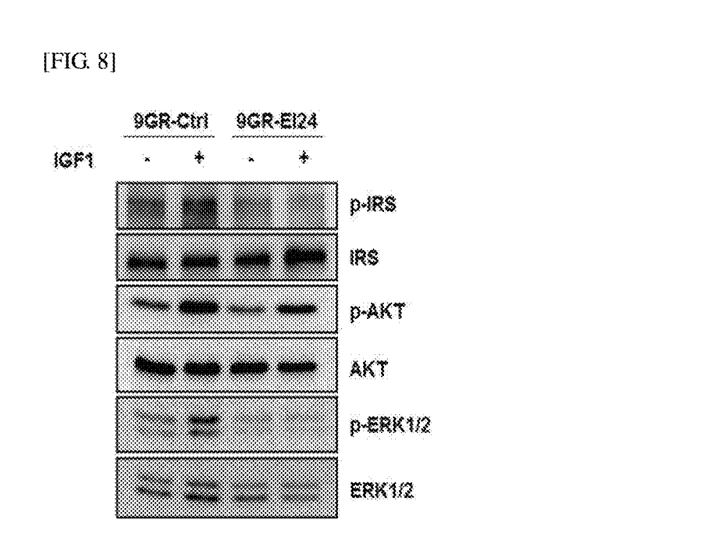
FIG. 8 illustrates analysis results of an effect of EI24 on IGF-1R signaling.

Based on the above-described results, an effect of IGF1 treatment was measured by Western blotting using 9GR cells and a cell line obtained by overexpressing EI24 in the 9GR cells. As a result, no increase in the expression of phosphorylated IRS and ERK1/2 was discovered, from which it is confirmed that overexpression of the EI24 gene actually inhibited the IGF-1R signaling pathway by IGF-1 in non-small cell lung cancer cell lines (see FIG. 8).

Figure 9:
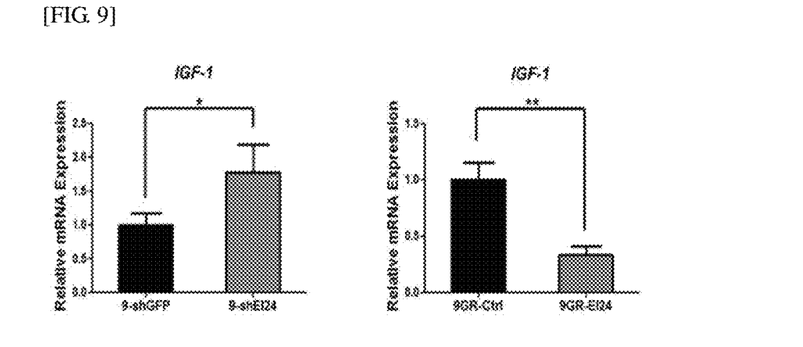
FIG. 9 illustrates reverse transcription polymerase chain reaction (RT-PCR) analysis results of an effect of an expression level of EI24 on an expression level of IGF-1.
Figure 10:
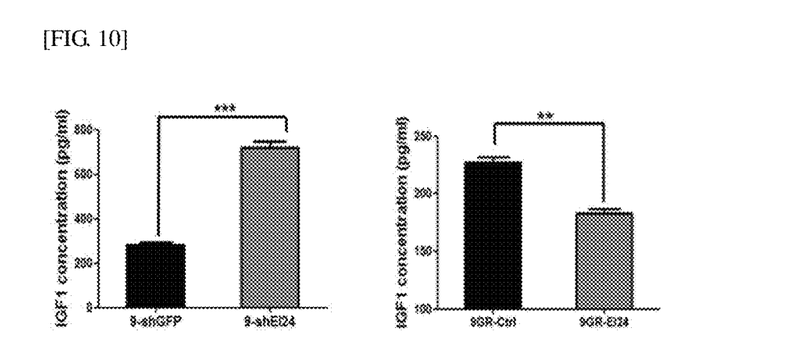
FIG. 10 illustrates enzyme-linked immunosorbent assay (ELISA) results of an effect of an EI24 expression level on an IGF-1 expression level.

Results in protein expression were discovered, and thus the amount of mRNA of IGF-1 was measured by RT-PCR to examine whether it also affects transcriptional regulation. As a result, it was discovered that expression changes of EI24 regulated the expression of mRNA of IGF-1 acting as a key ligand in the activation of IGF-1R (see FIG. 9), and the concentration of IGF-1 was actually changed in cell lines according to an expression amount of EI24 (see FIG. 10). These are measurement results of the amount of IGF-1 present in a medium obtained from a cell line by an enzyme-linked immunosorbent assay (ELISA, R&D Systems #DG100).

<Example 3> Analysis of Drug Resistance Mechanism According to Reduced EI24 Expression To examine whether a drug resistance acquisition process due to reduced EI24 expression is associated with cancer stem cells, an experiment for cancer stem cell-specific markers (NANOG and SOX-2) was performed using RT-PCR.

Figure 11:
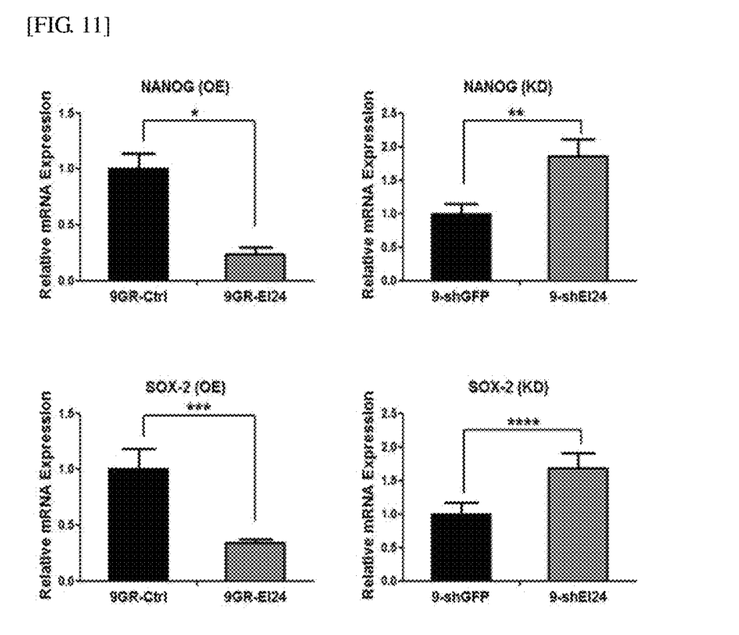
FIG. 11 illustrates analysis results of expression levels of cancer stem cell markers according to EI24 expression.

As a result, it was observed that increased cancer stem cell-specific markers were changed according to the expression amount of EI24 in cell lines in which the expression of EI24 was reduced (see FIG. 11).

Figure 12:
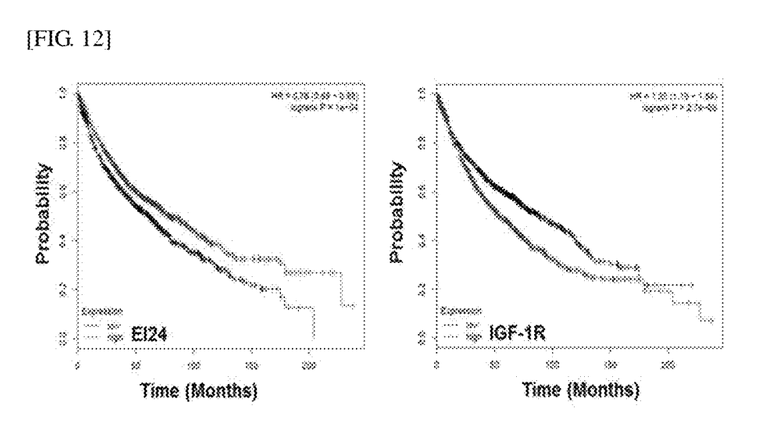
FIG. 12 illustrates analysis results of an effect of expression levels of EI24 and IGF-1R on prognosis of cancer patients.

<Example 4> Analysis of Expression Levels of EI24 and IGF-1R on Survival Rates of Lung Cancer Patients Survival rates of lung cancer patients according to expression amounts of EI24 and IGF-1R were compared through the GEO2R interface using the GSE38121, GSE38404, and GSE37700 datasets obtained from Gene Expression Omnibus (www.ncbi.nlm.nih.gov/geo) and, as a result, a poor prognosis was observed in patient groups showing relatively low expression of EI24 and high expression of IGF1-R (see FIG. 12).

<Example 5> Evaluate Effectiveness of IGF-1R Inhibitor

Figure 13:
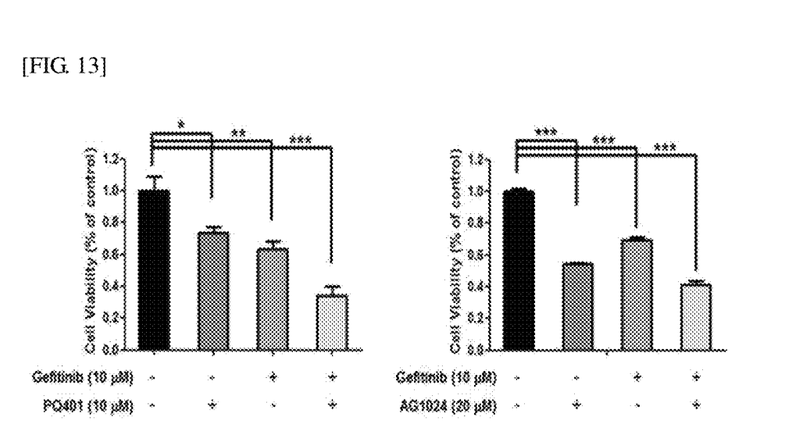
FIG. 13 illustrates analysis results of an effect of EGFR-TKI and IGF-1R inhibitors on cell viability of lung cancer cells.
Figure 14:
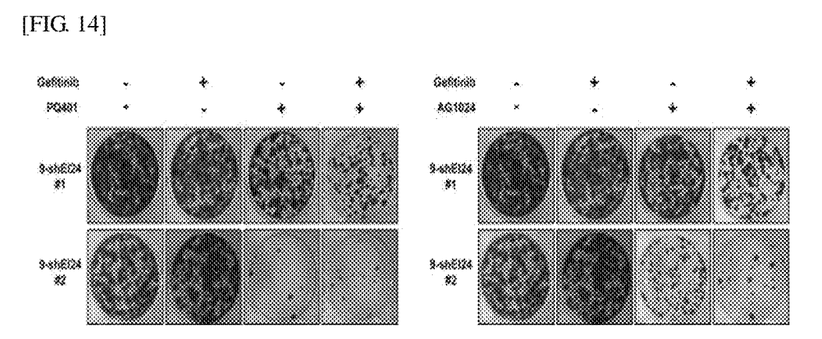
FIG. 14 illustrates analysis results of an effect of EGFR-TKI and IGF-1R inhibitors on the carcinogenic ability of lung cancer cells.

As such, it was verified that the acquired resistance to EGFR-TKI according to reduced EI24 expression was due to IGF-1R in non-small cell lung cancer cell lines. To investigate the efficacy of IGF-1R-targeted treatments, after treatment with EGFR-TKI, an IGF-1R inhibitor, or the two inhibitors at the same time, survival rates of PC9 cells with reduced expression of EI24 were compared with one another. As a result, it was confirmed that EGFR-TKI-resistant cell lines, obtained by reducing the expression of EI24 in PC9, which is an EGFR-TKI-sensitive cell line, exhibited more effective apoptosis when simultaneously treated with gefitinib and two IGF-1R inhibitors than when treated with each thereof (FIG. 13). In addition, a colony formation assay of these cell lines was performed and, as a result, it was confirmed that the cell lines also had a significantly reduced carcinogenic ability (FIG. 14).

Figure 15:
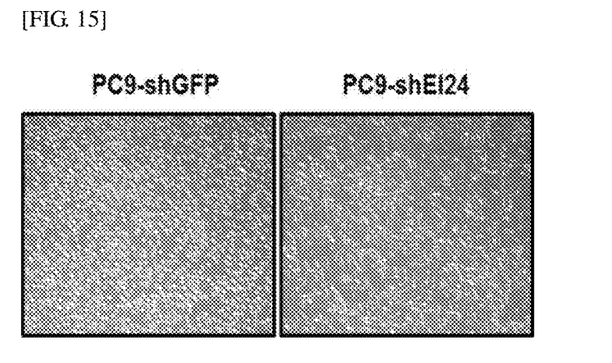
FIG. 15 illustrates comparison results of cell morphology of cell lines according to reduced EI24 expression.

PC9, which is a non-small cell lung cancer cell line, exhibits a typical epithelial morphology, but is converted to a mesenchymal-like cell line through epithelial to mesenchymal transition (EMT) when the expression of EI24 is reduced, and this was easily observed even by a general optical microscope (see FIG. 15).

Various studies have verified anti-cancer resistance mechanisms by the association of EMT with the activation of IGF-1R and therefore, when associated with existing research (EMT induction according to reduced EI24 expression) of the inventors of the present application, it is verified that IGF-1R-targeted treatments are effective.

According to the present disclosure, the presence or absence of resistance to anti-cancer drugs can be determined by detecting an expression level of EI24. In addition, resistance to anti-cancer drugs can be inhibited, delayed, or improved using EI24 or an activating agent thereof. Moreover, by regulating a pathway of 024-mediated resistance to anti-cancer drugs, the efficacy of existing anti-cancer drugs can be enhanced and resistance to anti-cancer drugs can be inhibited, delayed, or improved.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of diagnosing and treating EGFR-TKI drug resistance in an EGFR-TKI drug-administered patient, the method comprising:

contacting a biological sample from an EGFR-TKI drug-administered patient with an antibody specifically binding to an EI24 protein and an antibody specifically binding to an insulin growth factor-1 (IGF-1) protein and detecting an expression level of the EI24 protein and the IGF-1 protein in the biological sample by detecting the antibody binding to the EI24 protein and to the IGF-1 protein;

diagnosing the EGFR-TKI drug-administered patient as having EGFR-TKI drug resistance when the expression level of the EI24 protein is 5 times to 20 times lower than that of a control sample obtained from an EGFR-TKI drug resistance-free control group and the expression level of the IGF-1 protein is greater than that of a control sample obtained from an EGFR-TKI drug resistance-free control group; and administering an effective amount of EI24 and at least one selected from the group consisting of EGFR-TKI and an insulin growth factor-1 receptor (IGF-1R) inhibitor to the patient diagnosed as having EGFR-TKI drug resistance.

2. The method of claim 1, wherein the EGFR-TKI comprises at least one selected from the group consisting of erlotinib, lapatinib, apatinib, neratinib, poziotinib, and gefitinib.

3. The method of claim 1, wherein the IGF-1R inhibitor comprises at least one selected from the group consisting of OSI-906, NVP-AEW541, GSK1904529A, NVP-ADW742, BMS-536924, NT157, AG-1024, GSK1838705A, BMS-754807, PQ401, and picropodophyllin.

* * * * *